US008894580B2

(12) United States Patent
Kisner et al.

(10) Patent No.: US 8,894,580 B2
(45) Date of Patent: Nov. 25, 2014

(54) REFLECTIVE ECHO TOMOGRAPHIC IMAGING USING ACOUSTIC BEAMS

(71) Applicant: UT-Battelle, LLC, Oak Ridge, TN (US)

(72) Inventors: Roger Kisner, Knoxville, TN (US);
Hector J. Santos-Villalobos, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 13/870,604

(22) Filed: Apr. 25, 2013

(65) Prior Publication Data

US 2013/0286778 A1   Oct. 31, 2013

Related U.S. Application Data

(60) Provisional application No. 61/639,247, filed on Apr. 27, 2012, provisional application No. 61/779,254, filed on Mar. 13, 2013.

(51) Int. Cl.
*A61B 8/14*     (2006.01)
*G01V 1/46*     (2006.01)
*G01S 15/89*    (2006.01)
*G01N 29/00*    (2006.01)
*G01N 29/06*    (2006.01)
*G01N 29/26*    (2006.01)

(52) U.S. Cl.
CPC . *G01V 1/46* (2013.01); *G01S 15/89* (2013.01); *G01N 29/00* (2013.01); *G01S 15/8915* (2013.01); *G01S 15/8927* (2013.01); *G01N 29/069* (2013.01); *G01N 29/262* (2013.01); *G01S 15/8977* (2013.01); *G01S 15/8913* (2013.01); *G01N 2291/106* (2013.01)

USPC ............. 600/443; 382/182; 367/87; 367/119

(58) Field of Classification Search
USPC ....................................................... 382/182
See application file for complete search history.

(56) References Cited

U.S. PATENT DOCUMENTS

| 5,717,169    | A   |   | 2/1998  | Liang et al.              |
|--------------|-----|---|---------|---------------------------|
| 6,221,020    | B1  | * | 4/2001  | Lysyansky et al. ... 600/453 |
| 2002/0138000 | A1  | * | 9/2002  | Rather et al. ....... 600/407 |
| 2002/0143245 | A1  | * | 10/2002 | Rather et al. ....... 600/407 |
| 2008/0262351 | A1  | * | 10/2008 | Scampini .......... 600/443 |
| 2008/0306382 | A1  | * | 12/2008 | Guracar et al. ...... 600/437 |
| 2010/0140486 | A1  | * | 6/2010  | Idoine ............ 250/363.06 |
| 2010/0249594 | A1  | * | 9/2010  | Magee ............. 600/443 |

(Continued)

OTHER PUBLICATIONS

Brown et al., "Automatic panoramic image stitching using invariant features," International Journal of Computer Visions (2007) 74(1): 59-73.

(Continued)

*Primary Examiner* — Ian J Lobo
*Assistant Examiner* — Hovhannes Baghdasaryan
(74) *Attorney, Agent, or Firm* — Novak Druce Connolly Bove + Quigg LLP

(57) ABSTRACT

An inspection system includes a plurality of acoustic beamformers, where each of the plurality of acoustic beamformers including a plurality of acoustic transmitter elements. The system also includes at least one controller configured for causing each of the plurality of acoustic beamformers to generate an acoustic beam directed to a point in a volume of interest during a first time. Based on a reflected wave intensity detected at a plurality of acoustic receiver elements, an image of the volume of interest can be generated.

4 Claims, 12 Drawing Sheets

(56) References Cited

U.S. PATENT DOCUMENTS

2010/0249596 A1* 9/2010 Magee .................... 600/447
2010/0280381 A1* 11/2010 Madore .................... 600/447
2011/0245750 A1* 10/2011 Lynch et al. ................ 604/5.01

OTHER PUBLICATIONS

Chang et al., "Coded aperture imaging of Gamma-Rays using multiple pinhole arrays and multiwire proportional chamber detectors," Nuclear Science, IEEE Transactions (1975) 22(1): 374-678.

Juan et al., "A comparison of SIFT, PCA-SIFT and SURF," International Journal of Image Processing (2009) 3(4): 143-152.

Krause et al., "Ultrasonic imaging of concrete elements: State of the art using 2D synthetic aperture," Non-Destructive Testing in Civil Engineering (2003). Retrived Jun. 3, 2013, from http://www.ndt.net/article/ndtce03/papers/v051/v051.htm.

Levin et al., "Image and depth from a conventional camera with a coded aperture," ACM Transactions on Graphics (2007) 26(3): Article 70.

Mu et al., "Aperture collimation correction and maximum-likelihood image reconstruction for near-field coded aperture imaging of single photon emission computerized tomography," Medical Imaging, IEEE Transaction (2006) 25(6): 701-711.

Ogunsola et al., "Modelling shielding properties of concrete," 17th International Zurich Symposium on Electromagnetic Compatibility (2006): 34-37.

Sato et al., "Measurement of the complex refractive index of concrete at 57.5 GHz," IEEE Transactions on Antennas and Propagation (1996) 44(1): 35-40.

Sbartai et al., "Concrete moisture assessment using radar NDT technique—Comparison between time and frequency domain analysis," Non-Destructive Testing in Civil Engineering Nantes, France (Jul. 2009). (8 pages).

Schickert, "Progress in ultrasonic imaging of concrete," Materials and Structures (Nov. 2005) 38:807-815.

Schickert et al., "Ultrasonic imaging of concrete elements using reconstruction by synthetic aperture focusing technique," Journal of Materials in Civil Engineering (Jun. 2003) 15(3): 235-246.

Weiss "Non redundant point distribution for coded aperture imaging with application to three-dimensional on-line x-ray for information retrieving," Computers, IEEE Transactions (1975) C-25(4): 391-394.

* cited by examiner

100

400

1000

1000

REFLECTIVE ECHO TOMOGRAPHIC IMAGING USING ACOUSTIC BEAMS

CROSS-REFERENCE TO RELATED APPLICATIONS

This application claims priority to and the benefit of U.S. Provisional Application No. 61/639,247, entitled "REFLECTIVE ECHO TOMOGRAPHIC IMAGING USING PHASED ARRAYS" and filed Apr. 27, 2012, and U.S. Provisional Application No. 61/779,254, entitled "RECONSTRUCTION TECHNIQUES FOR REFLECTIVE ECHO TOMOGRAPHIC IMAGING USING PHASED ARRAYS" and filed Mar. 13, 2013, the contents of which are both herein incorporated by reference in their entirety.

GOVERNMENT LICENSE RIGHTS

This invention was made with government support under contract no. DE-AC05-00OR22725 awarded by U.S. Department of Energy. The government has certain rights in the invention.

FIELD OF THE INVENTION

The present invention relates to inspection systems, and more specifically to apparatus and methods for inspecting structures using acoustic beams to identify anomalies therein.

BACKGROUND

In many industries and applications, a common method for constructing a structure is to form cement support structures and attach thereto a covering or lining layer of metal, such as steel. In at least some applications, there is a need to inspect the cement support structures that are hidden behind steel (and other metal) plates and tubes. For example, in the case of gas and oil industries, steel/cement structures are commonly utilized to form pipelines and conduits for gas and oil wells. That is, after the well is drilled, a cement layer is disposed on the rock face of the well (to provide a grout) and a steel (or other metal) casing is positioned on the cement to provide to define the interior of the well. In these cases, there is a critical need for inspection of these components to verify the integrity of the grout and the casing, as a failure in either of these can lead to contamination of the environment (e.g., contamination of the water table). Ideally, such an inspection would include determining (1) whether grout has de-bonded from the casing, (2) location of cracks, voids, fissures, or other anomalies and defects in the grout and the casing, (3) the shape and position of the anomalies and defect, (4) a depth or thickness of grout, and (5) presence of water or other fluids between the rock face and the casing.

Ultrasonic inspection methods have been used for pipeline and wellbore inspections for some time. An example of one commonly used inspection system is described in U.S. Pat. No. 5,717,169 to Liang et al., issued Feb. 10, 1998. However, methods for examining cement-type structures generally require access to two sides of the cement structure, a near impossibility in the case of oil and gas wells. As such, ultrasonic inspection methods in these industries are generally limited to an examination of the steel casing for flaws. Another difficulty in the case of ultrasonic inspection of oil and gas wells is that de-bonding of the cement from the steel casing can prevent penetration of acoustic waves from the steel to cement, because of air gap in between. A further problem is that the density and porosity of grout materials, such as cement, is highly variable and strongly affects the attenuation. For example, higher porosity results in more signal being lost through the porous material.

SUMMARY

Embodiments of the invention concern systems and method for inspection of structures. In a first embodiment of the invention, an inspection system is provided. The inspection system includes a plurality of acoustic beamformers, each of the plurality of acoustic beamformers comprising a plurality of acoustic transmitter elements. The system also includes at least one controller configured for causing each of the plurality of acoustic beamformers to generate a plurality of acoustic beams directed to a point in a volume of interest during a first time and to generate an image of the volume of interest based on reflected waves associated with the plurality of acoustic beams.

In the system, the at least one controller can cause each one of the plurality of acoustic beamformers to generate each one of the plurality of acoustic beams by operating the plurality of acoustic transmitter elements in the one of the plurality of beamformers using at least one of different timings and different phases among the plurality acoustic transmitter elements.

The system can also include a plurality of acoustic receiver elements. In some cases, the acoustic receiver elements are intermixed among the plurality of acoustic transmitter elements. In other cases, at least a portion of the acoustic transmitter elements comprise acoustic transceiver elements which define the plurality of acoustic receiver elements.

In the system, the at least one controller can be further configured for operating at least one of the plurality of acoustic beamformers during a first time and obtaining, during a second time after the first time, echo signals corresponding to a reflected wave intensity detected at the plurality of acoustic receiver elements. The at least one controller can also be further configured for repeating the operating and the obtaining for a plurality of other points in the volume of interest and combining the echo signals for all points in the volume of interest to yield combined signals and generating an image of the volume of interest based on the combined signals. In some configurations, the generating includes applying a coded aperture reconstruction algorithm for the generating of the image, and wherein the shadowgram for the coded aperture reconstruction algorithm is based on the combined signals and a pattern of the plurality of acoustic receiver elements.

In a second embodiment of the invention, a method of inspecting of a volume of interest, including a substrate, a grout disposed on the substrate, and a casing disposed on the grout, is provided. The method includes illuminating, during one or more first times, a plurality of points in a volume of interest by directing a plurality of acoustic beams from a plurality of acoustic beamformers to each of the plurality of points and obtaining, during one or more second times after the first times, echo signals corresponding to a reflected wave intensity detected at the plurality of acoustic receiver elements. The method also includes combining the echo signals for all points in the volume of interest to yield a combined signals and generating an image of the volume of interest based on the combined signals.

In the method, each of the plurality of acoustic beamformers can include a plurality of acoustic transmitter elements and the illuminating can include operating the plurality of acoustic transmitter elements with at least one of different timings and different phases among the plurality of acoustic transmitter elements.

The method can also include identifying sub-structures in the grout and a boundary between the grout and the substrate based on the echo signals the generating can further include adjusting reconstruction parameters based on the sub-structures and the boundary, estimating an attenuation of the sub-structures, and deriving the image based on the attenuation of the sub-structures and the boundary.

In the method, the identifying of the boundary can include determining a location of the boundary by identifying the portion of the plurality of points associated with a change in the reflected wave intensity corresponding to a change in indices of refraction for the grout and the substrate. Further, the determining can include repeating the illuminating and obtaining for additional points between the portion of the plurality of points and adjusting the location based on the signals from the additional points.

In the method, the identifying of the sub-structure can include determining a location of a sub-structure in the grout and the substrate by identifying the portion of the plurality of points associated with attenuation in the acoustic wave intensity. Further, the determining can include repeating the illuminating and obtaining for additional points between the portion of the plurality of points and adjusting the location based on the signals from the additional points.

In the method, the generating can include applying a coded aperture reconstruction algorithm for the generating of the image, where the shadowgram for the coded aperture reconstruction algorithm is based on the combined signals and a pattern of the plurality of acoustic receiver elements. Alternatively, the generating can include applying a filtered back projection reconstruction algorithm.

In a third embodiment of the invention, there is provided a system for inspecting a well defined by a substrate, a grout disposed on the substrate, and a casing disposed on the grout and defining an interior well wall. The system can include a carriage removably attachable to the interior well wall and include a plurality of acoustic beamformers and a plurality of receiver elements, where each of the plurality of acoustic beamformers includes a plurality of acoustic transmitter elements. The system can also include at least one controller configured for causing each of the plurality of acoustic beamformers to generate an acoustic beam directed to a point in a volume of interest during a first time, to obtain, during a second time after the first time, echo signals corresponding to a reflected wave intensity detected at the plurality of acoustic receiver elements, and to repeat the transmitting and the obtaining for a plurality of other points in the volume of interest.

In the system, the at least one controller is further configured for combining the echo signals for all points in the volume of interest to yield combined signals and for generating an image of the volume of interest based on the combined signals.

Further, the at least one controller can be configured to cause each one of the plurality acoustic beamformers to generate the acoustic beam by operating the plurality of acoustic transmitter elements in the one of the plurality of beamformers using at least one of different timings and different phases among the plurality of acoustic transmitter elements.

In the system, at least a portion of acoustic transmitter elements comprise acoustic transceiver elements, wherein the acoustic transceiver elements define the plurality of acoustic receiver elements.

DETAILED DESCRIPTION

Figure 1:
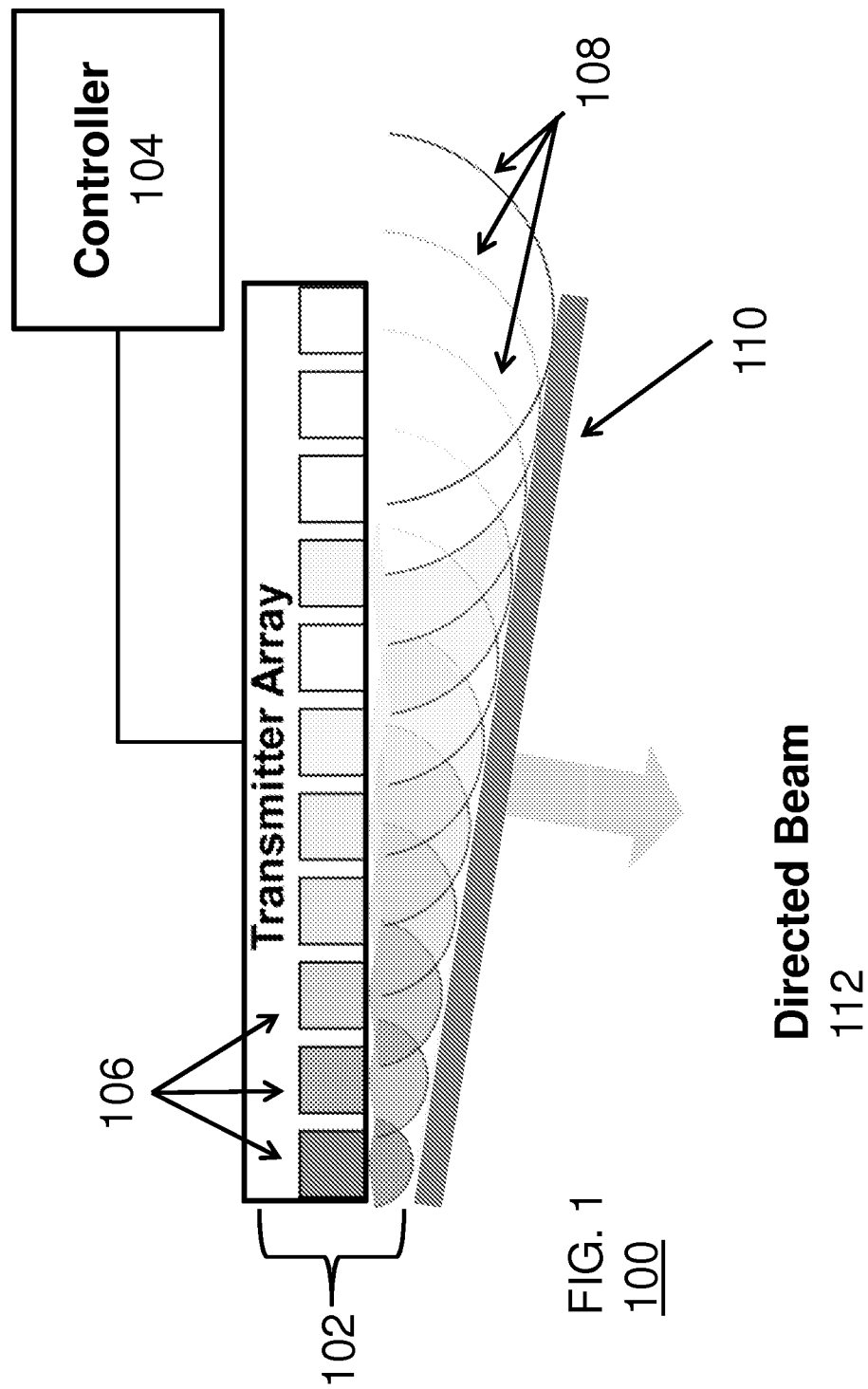
FIG. 1 is a schematic diagram of a acoustic beamformer in accordance with the various embodiments.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

To overcome porosity, scattering, and partial blockage constraints in existing inspection methods, the various embodiments are directed to a new system and method for inspection of structures such as those described above. In particular, the various embodiments are directed to a new configuration of acoustic transmitters and associated electronics, coupled with image reconstruction software that permits a tomographic reconstruction of grout features that lie beneath a casing, such as a metal casing. In the various embodiments, such features can include localization and visualization of the substrate surface on which the grout is disposed (e.g., a rock surface), identification of debonded regions, and localization and visualization of anomalies and defects in the grout.

In the various embodiments, the acoustic transmitters are arranged and configured to form a plurality of acoustic beamformers, where each acoustic beamformer is capable of generating a beam of acoustic waves that can be directed to illuminate to a same point in a volume of interest (e.g., a point in the grout beneath the casing). That is, a point is "illuminated" by causing the beams from the various beamformers to intersect at the point (i.e., the wave intersection volume). Further, the acoustic transmitters are arranged and configured to allow the illuminated point in the volume of interest to vary (i.e., to scan the volume of interest). In operation, as the volume of interest is scanned, waves reflected from the intersection volume (i.e., reflected waves or echoes) return to one or more receivers and can be used to generate echo signals corresponding to the reflected wave intensity detected. These echo signals at the receivers can then be used to create an image of the volume of interest or otherwise generate data regarding the volume of interest.

In the various embodiments, the beams are generated using multiple arrays at different locations, where each array is a beamformer defined by multiple transmitters. That is, an array of arrays. In operation, an array can use at least the timing or phase of signals sent to the transmitters to generate a directed acoustic beam with an angle determined by the programming of the signals to the transmitters. Multiple individual arrays can be assembled to form an equivalent large array that is also controllable. As a result, coherent energy can be focused on a single spot by beams crossing, thus increasing the total signal strength. In the various embodiments, a large number of beams would be utilized. For example, between 4 and 5000 beams can be utilized, such as between 25 and 100 beams. A large number of beams can be used so blockages and scattering will not significantly affect collection of useful image data.

As noted above, one aspect of the various embodiments is to provide acoustic beamformers for generating directed acoustic beams of acoustic waves. The configuration and operation of such a beamformer is described below with respect to FIG. 1. FIG. 1 is a schematic diagram of an acoustic beamformer 100 in accordance with the various embodiments. As shown in FIG. 1, the acoustic beamformer 100 includes a transmitter array 102 associated with a controller 104.

The transmitter array 102 includes, as shown in FIG. 1, an array of individual transmitter elements 106. Each of the transmitter elements 106 can be configured to produce acoustic waves 108 suitable for ultrasonic inspection. For example, in one embodiment, the transmitter elements 106 can each be configured to generate acoustic waves in the range of 1 MHz to 10 MHz. Further, the signals sent to the transmitter elements 106 can be a short duration pulses. Other implementations are possible such as a gated sine wave (or Gabor function). However, a pulse system will excite all modes while the sine wave excites only specific oscillation modes near the resonance of the sine wave and its harmonics.

In some embodiments, at least a portion of the transmitter elements can have a wide band frequency response while others have a narrow band response. For those transmitter elements having a wide band frequency response, some amount of frequency shift or modulation is possible so that frequency sweeping or chirping is feasible. However, for transmitter elements that are high Q (and therefore have a narrow frequency operating band) only one resonant frequency of operation is possible. For these high Q transducers, the amplitude and timing of excitation are the only methods of modulation available. The benefit of wide band transmitter elements is the ability to modulate excitation frequency and therefore avoid exciting unwanted resonances in the volume that acoustic energy is traveling. However, the high Q transducers exhibit higher gain and signal-to-noise ratios, which might be beneficial in some applications such as where high background noise is present or the return acoustic signals are highly attenuated. The choice of transmitter element frequency response can balance these factors for each application.

It is worth noting that the high Q versus broadband characteristic can also apply to receiver elements and to devices that are used in both modes.

In the specific case of oil and gas wells and piping, the ultrasonic transducers (i.e., transmitter and receiver elements) can be configured for long-term operation at elevated temperatures (up to 150 degrees C. and sometimes to 200 degrees C.). Similarly, the ability to function in a high-pressure environment may also necessary. Pressures exceeding 5000 psi can be encountered at depths of 10,000 feet. Thus, transducer elements must be capable of full function at those and higher pressures.

The controller 104 is configured to control the operation of the transmitter elements 106 to generate a directed acoustic beam. In particular, the phase, timing, amplitude, frequency, pulse rate and other output characteristics of the transmitter elements 106 in the transmitter array 102 can be selected to form the wavefront 110 defining the directed acoustic beam 112. In particular, the wavefront 110 is defined via the constructive and destructive interference of the acoustic waves 108 from the individual transmitter elements 106. Thus, by adjusting the output characteristics of the transmitter elements 106, the controller 104 is capable of causing the transmitter array 102 to generate a directed acoustic beam 112 traveling in a desired direction.

Although the transmitter elements 106 in transmitter array 102 are shown to be placed in a single row and equally spaced apart, the various embodiments are not limited in this regard. Rather, the transmitter elements 106 for acoustic beamformer 100 can be placed in any type of arrangement, including two- and three-dimensional arrays of transmitter elements, with a same or different spacing between transmitter elements. Further, the transmitter elements 106 need not be identical. Rather, the transmitter elements 106 can be selected to have different output characteristics.

Figure 2:
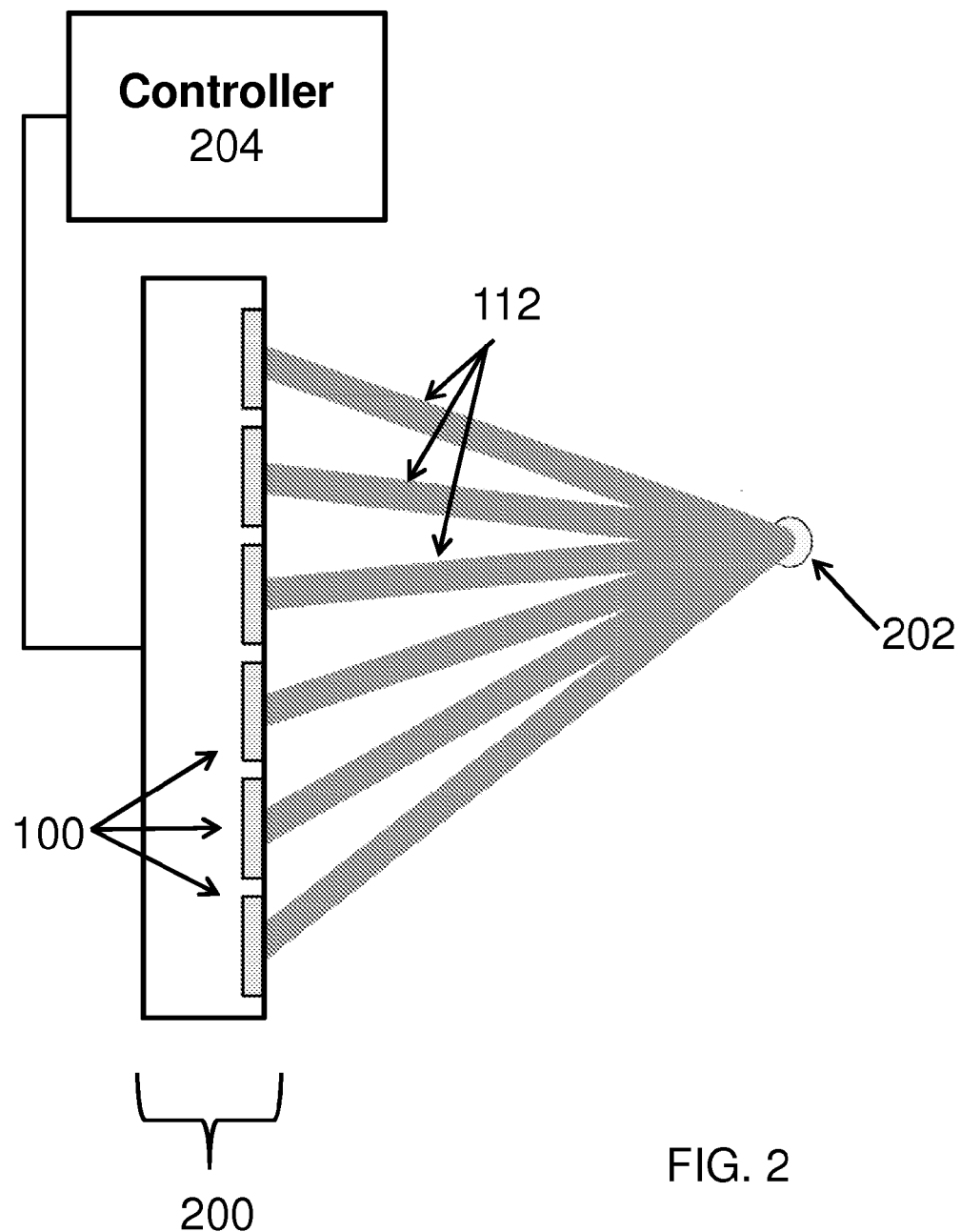
FIG. 2 is a schematic diagram of a beamformer array in accordance with the various embodiments.

As noted above, to illuminate a point in a volume of interest, multiple beams are directed to the same point. This can be accomplished using a beamformer array, as shown in FIG. 2. FIG. 2 is a schematic diagram of a beamformer array 200 in accordance with the various embodiments. The beamformer array 200 includes, as shown in FIG. 2, an array of individual acoustic beamformers 100, such as those described above with respect to FIG. 1.

In operation, each of the acoustic beamformers 100 can generate a directed acoustic beam 112 to illuminate a spot 202, as illustrated in FIG. 2. In some embodiments, an illumination controller 204 can be provided to manage operation of the beamformer array 200. The illumination controller 204 can be a part of the control logic for the inspection system into which the beamformer array 200 is integrated with. In some embodiments, the illumination controller 204 can be configured to control each of the transmitter elements 106 in each of the acoustic beamformers 100 to coordinate operation and cause the multiple beams 112 to be generated. In other embodiments, the illumination controller 204 can be a supervisory controller operating in conjunction with individual controllers associated with each of the acoustic beamformers. In such a configuration, the illumination controller 204 can provide instructions for illuminating a particular point in the volume of interest and the individual controllers can include logic for individually configuring a corresponding one of acoustic beamformers 100 to provide the desired illumination. Alternatively, the illumination controller 204 can provide individual instructions to each acoustic beamformer 100 to produce a beam with particular output characteristics and a direction and the individual controllers can include logic for individually configuring a corresponding one of acoustic beamformers 100 to provide the required beam.

Although the acoustic beamformers 100 in beamformer array 200 are shown to be placed in a single row and equally spaced apart, the various embodiments are not limited in this regard. Rather, the acoustic beamformers 100 for beamformer array 200 can be placed in any type of arrangement, including two- and three-dimensional arrays of acoustic beamformers, with a same or different spacing between acoustic beamformers. Further, the acoustic beamformers 100 in beamformer array 200 need not be identical. Rather, the acoustic beamformers 100 in beamformer array 200 can be configured to have different output characteristics.

In some embodiments, the beamformers 100 may not be defined a priori. That is, the beamformer array 200 can be formed using a single array of transmitter elements. The illumination controller 204 can then be configured to operate different portions of this single array as different beamformers. In some cases, the different beamformers can even share transmitter elements. Such a configuration can be utilized in various circumstances. For example, if the size of sub-structures varies significantly in the grout, differently sized beams may be needed to obtain appropriate echo signals for such sub-structures. Thus, by allowing the illumination controller to adjust the transmitter elements defining a beamformer, differently sized beams can be provided. In another example, the grout may have a large number of sub-structures therein. Thus, if a small number of beams are provided, blockages and scattering may result in a low incoming reflected wave intensity. Thus, the reflected wave intensity can be increased (and thus the echo signal) by providing a larger number of beams.

In some embodiments, the transmitter elements can be utilized to both generate and detect acoustic waves. For example, the transmitter elements 106 in each of acoustic beamformers 100 can be implemented as a transceiver and operated by controller 104 to alternate between operation as a transmitter and operation as a receiver. The timing for such alternating can be selected based on the output characteristics of the transmitter elements 106, the properties of the volume of interest, and the point of interest being illuminated. That is, the operation needs to be adjusted to provide sufficient time for the reflected signals from the illuminated points to reach the transmitter elements 106 so that a useful echo signal can be generated by the transceiver. For example, the transmission and reception processes can be accomplished using single devices by gating the amplifiers according to the reflected wave timing. In such configurations, the transceiver should also be suitably sensitive to incoming waves when operating in receiver mode.

In other embodiments, separate receiving elements (not shown in FIGS. 1 and 2) can be included in the beamformer array. The locations of these receiving elements can coincide with the locations of the transmitter elements, however the various embodiments are not limited in this regard. Rather, the receiving elements can be arranged in a one-, two-, or three-dimensional array that is different from the arrangement of the transmitter elements 106 in the beamformer array. Again, a signal timing can be provided to ensure that useful signals are received.

In an alternative embodiment, one could drive the transmitter elements continuously with carefully planned frequency or phase differences and look for interference patterns. However, such an implementation can be more difficult because it is necessary to send and receive simultaneously. For example, such an implementation would require separate transmit and receive elements. The receiver elements can be the exact same type of transducer as the transmitter elements and be located adjacent to the transmitter elements. An exemplary arrangement would be to provide alternating transmitter and receiver elements in a two-dimensional array. Such components can be permanently set to these functions or can be determined by software (and their associated hardware). The latter implementation is more flexible and can be reconfigured to function in many modes of operation by the software system.

Figure 3A:
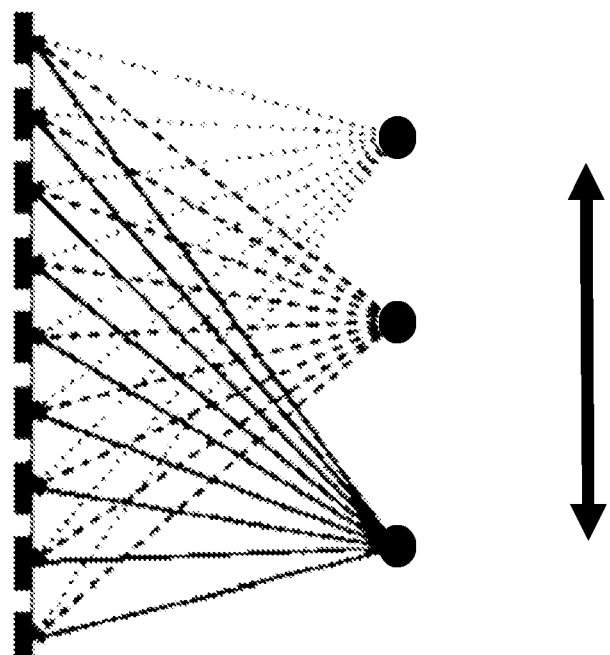
FIGS. 3A and 3B illustrate lateral and vertical scanning in accordance with the various embodiments.
Figure 3B:
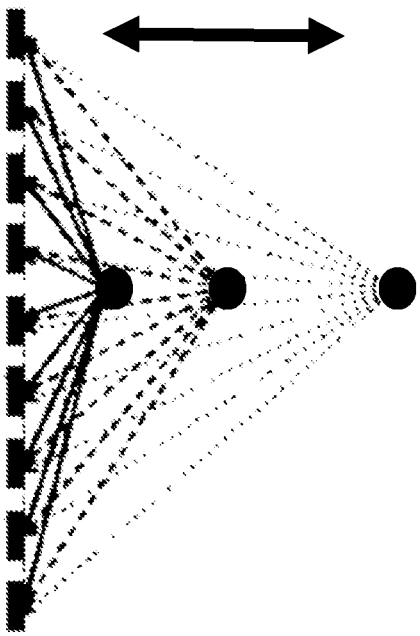

Using the configuration of FIGS. 1 and 2, a beamformer array can therefore be provided that is capable of scanning a volume of interest. For example, the angles of all of the directed acoustic beams can be adjusted to provide a lateral scan (with respect to the beamformer array), as shown in FIG. 3A, or to provide a vertical scan (with respect to the beamformer array, as shown in FIG. 3B.)

Using data from such scans, another aspect of the various embodiments is to generate a visualization of the underlying grout by combining techniques from confocal microscopy and computational tomography (CT). An exemplary methodology for doing so is illustrated in FIG. 4.

Figure 4:
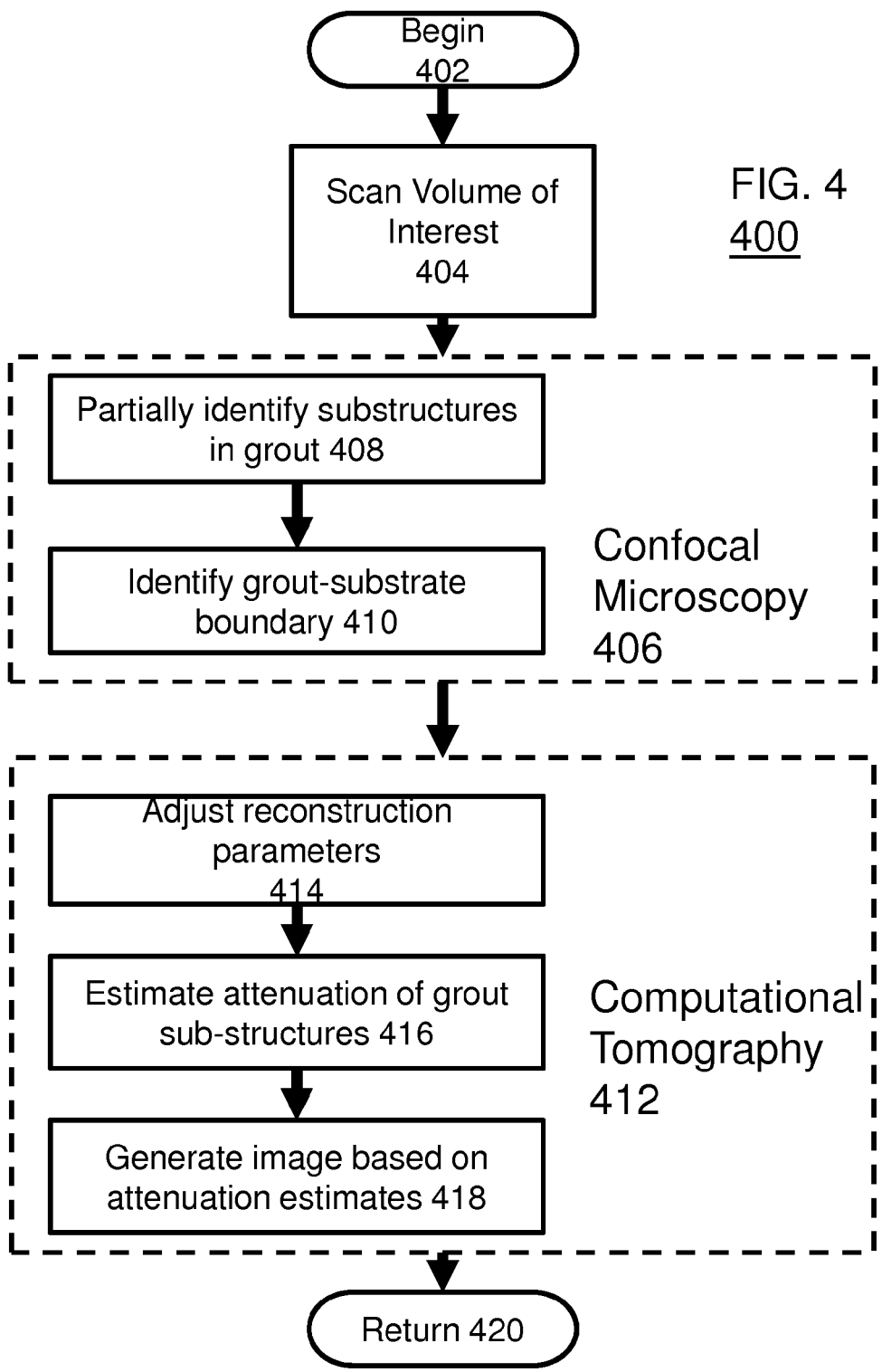
FIG. 4 is a flowchart of steps in an exemplary method for visualization and localization of defects and anomalies in accordance with the various embodiments.
Figure 5:
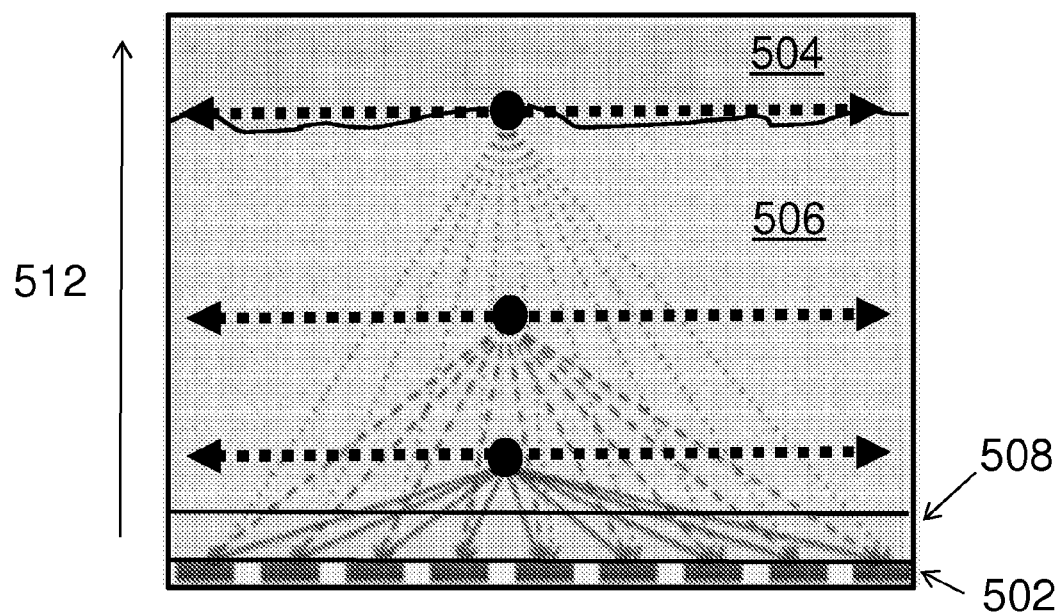
FIG. 5 illustrates detection of a boundary between grout and a substrate in accordance with the various embodiments.

FIG. 4 is a flowchart of steps in an exemplary method 400 for visualization and localization of defects and anomalies in accordance with the various embodiments. The method 400 begins at step 402 and continues on to step 404. At step 404, the volume of interest is scanned. For example, as illustrated above with respect to FIGS. 3A and 3B, the acoustic beamformers are configured to illuminate a plurality of points in the volume of interest. This is more clearly illustrated with respect to FIG. 5. As shown in FIG. 5, a beamformer array 502 is provided to scan a volume of interest 504 consisting of a substrate 504 (e.g., rock face), grout 506 (e.g., cement) disposed on the substrate 504, and a casing 508 (e.g., a metal plate) disposed on the grout 508. Thus, by adjusting the direction of the beams generated by beamformer array 502, the thickness of the grout can be scanned for a volume of interest. In some embodiments, the thickness of the grout may be known. Thus, the depth of scanning can be pre-defined or pre-selected and a direct, uniform scanning of the volume of interest can be performed and the same set of data can be used for the subsequent steps. However, in other embodiments, the scanning can be adjusted during the scanning, as described below, to identify certain features of the grout and substrate, as well as to more clearly define the boundary between the grout and the substrate.

Following or during the scanning of step 404, confocal microscopy steps are utilized to identify the locations of sub-sub-structures in the grout (step 406) and to identify the boundary between grout and substrate (step 408).

At step 406, confocal microscopy techniques can be used to identify de-bonding of the concrete and steel and at least the partial shape and size of strongly attenuating sub-structures (e.g., cracks, voids, fissures, etc.) and foreign substances in the grout, such as oil, gases, and water. At step 406, the identification of sub-structures can be identified by changes in reflected wave intensity. In general, when a point in the grout is illuminated, a portion of each beam focused on the point will be reflected and collected. However, when these beams are focused at a point at a boundary between the grout and the sub-structure or a point inside the sub-structure, the discontinuity at the boundary will result in changes in the intensity of the reflected waves. Thus, by detecting such changes, the locations of the sub-structures can be identified. Further, if multiple illuminated points correspond to such a boundary, a size and shape of the sub-structure may be ascertainable. As noted above, scanning may be fixed and uniform in some embodiments. However, in other embodiments, the scanning can be adjusted to obtain details on sub-structure boundaries. This is illustrated below with respect to FIG. 6.

Figure 6:
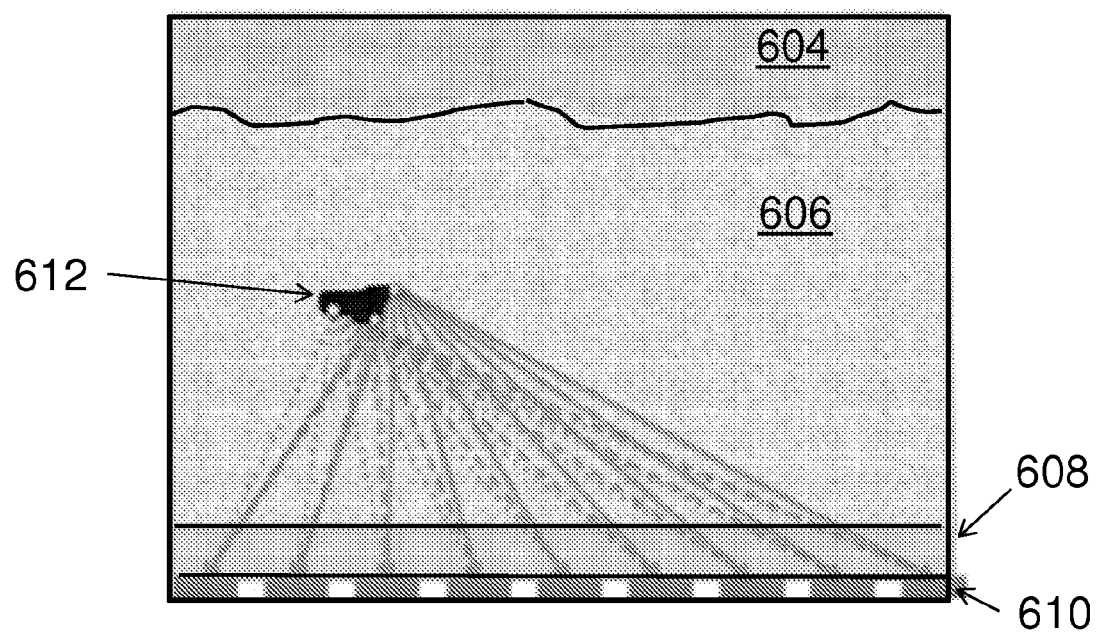
FIG. 6 illustrates detection of a sub-structure in the grout in accordance with the various embodiments.

FIG. 6 shows a beamformer array 610 that is provided to scan a volume of interest 604 consisting of a substrate 604 (e.g., rock face), grout 606 (e.g., cement) disposed on the substrate 604, and a metal plate 608 disposed on the grout 606. In operation, an initial scanning can be performed, as described above with respect to FIG. 5, where a uniform scan of the volume of interest is performed. For example a uniform grid of points with a first spacing can be provided. However, when a potential sub-structure 612 is detected (e.g., via changes in reflected wave intensity for the illumination of certain points in the grout 606), the scanning can be adjusted to obtain detailed data regarding the sub-structure 612. This can be performed in a variety of ways.

In one methodology, additional points can be illuminated, on a local or global basis. Thus, for at least the portion of the grout 606 associated with the sub-structure, a finer grid of points can be obtained to ascertain additional details regarding the size and shape of the sub-structure 612. In some embodiments, this can be done via a pre-defined selection of additional points. In other embodiments, an iterative process can be utilized. That is, increasingly finer grids of points can be generated (by adding additional points) until a condition is met. For example, if the size and shape determined by two consecutive iterations is within a pre-defined allowable difference.

In another methodology, the points surrounding the sub-structure 612 can be identified to define an area of interest. Thereafter, additional points can be added to reduce the area of interest iteratively. Upon a detection that a point is at a boundary between the sub-structure 612 and grout 606, that point is marked as defining a portion of the boundary. Additional points are then added until all the boundaries of the sub-structure are ascertained. Thereafter, the location and arrangement of these points can be utilized to identify the size and shape of the sub-structure 612.

Other methodologies for obtaining additional points to ascertain the size and shape of the sub-structure 612 can also be used in the various embodiments.

Similar to the process of step 406, the boundary between the grout and the underlying substrate can be identified at step 410. That is, when a point associated with a boundary between the grout and the underlying substrate is encountered, the reflected wave intensity will be altered by the discontinuity between the materials. Specifically, the reflected wave intensity would be altered in an amount corresponding to the difference between the indices of refraction between the grout and substrate. Based on the foregoing, the boundary can be ascertained in a variety of ways.

In some configurations, the boundary can be determined during the scan at step 404. In such a configuration, if the thickness of the grout is known or estimated (either based on construction or scan data), the scan at step 404 can be configured to provide additional points in portion of the volume of interest believed to include the boundary. For example, a finer grid of points can be provided in this portion than for other portions of the grout. Thereafter, the reflected wave intensity for these points can be considered to determine the boundary.

In other configurations, the boundary can be detected during scanning. For example, referring back to FIG. 5, the scanning can be performed in a direction 512. That is, points at progressively deeper depths are illuminated. Thus, as depth is increased, the reflection intensity of some points will be altered in response to reaching the boundary. In particular, the boundary between the grout 506 and the substrate 504 is found by increasing the scanning depth until a reflected wave intensity is detected that correlates to the difference in the index of refraction between the grout 506 and the substrate 504. As these changes are detected, these points can be marked as defining the boundary.

In some cases, scans at deeper locations (i.e., locations farther from beamformer array 502) may be distorted by additional voids and other structures at shallower locations (i.e., locations closer to beam array 502). Thus, the deeper region of interest can be occluded. Distortion can therefore be corrected by adjusting the measurements based on the material already scanned at shallower depths.

Following the confocal microscopy processes at 406, the method 400 can continue on to computational tomography (CT) processes at 412 to provide imaging of the grout. First, at step 414, the parameters for the CT process are adjusted based on the confocal scan data.

After step 406, a clear knowledge is obtained of the location of the substrate 504 relative to the beamformer array 502. Thus, one can define the size of the voxels (i.e., 3D grid) and the position of the sources. For 3D image reconstruction, the reconstruction area is represented by a 3D grid. The resolution of the system is defined by the distance between the 3D grid voxels. The reconstruction will estimate the attenuation of the material at each voxel. Note that if one is unable to discriminate attenuation changes inside the voxel—the voxel will contain an average attenuation of the material in it. The smaller the voxel the more it can be resolved. So, if the confocal microscopy approach shows that the concrete depth is half a meter and our system resolution is 1 mm, then one can set the grid depth to 500, 1 $mm^3$ voxels. Also, the CT reconstruction needs to know what is the path of the sound waves (i.e., where are the sources). This information is provided by the scanning step also.

Once the parameters for the CT process are adjusted at step 414, CT reconstruction can be performed. In particular, at step 416, the attenuation of the grout sub-structures can be estimated at step 416, based on the echo signals obtained based on the reflected wave intensity. The CT reconstruction assumes that a spot illumination is a point source, which reflects sound with fan or cone beam geometry. The grout volume is segregated in volume pixels (called voxels). These voxels will represent the localized attenuation power of the material. The iterative algorithm would then estimate the attenuation values for each voxel by back propagating the reflections of a set of spot illuminations, which should be located at the same depth. Some exemplary reconstruction methods for obtaining attenuation values are described below in greater detail with respect to FIGS. 7, 8, and 9. However, the various embodiments are not limited in this regard and any other reconstruction methods not described herein are equally suitable. The attenuation for each voxel can then be used to generate an image of the volume of interest at step 418. The method can then resume previous processing at step 420, including repeating method 400.

As noted above, various methodologies can be used to perform the CT reconstruction in the various embodiments. Some of these methods include, but are not limited to, coded aperture methods, coded source methods, and filtered back projection methods.

Coded Aperture Reconstruction. The idea behind coded apertures is that a known pattern (i.e., the coded mask) can be placed between the signal and the detector so that the signal generates a shadow of the coded mask at the detector, i.e., a shadowgram. If one assumes that there is no object between the source and the detector and that the source is infinitely small (e.g., a point source), the shadow at the detector will then be an exact copy of the coded mask shifted by the angular deviation of the source from the optical axis of the detector, one can formally express this as convolution:

$$P = \delta * M = M \tag{1}$$

where P is the shadowgram, δ is a Dirac delta function (i.e., a pulse) modeling the source, and M is the pattern of the coded mask. In some embodiments, the pattern can be generated by a physical interface (i.e., a mask) placed in front of the detector to attenuate the signal, as illustrated in FIG. 7.

Figure 7:
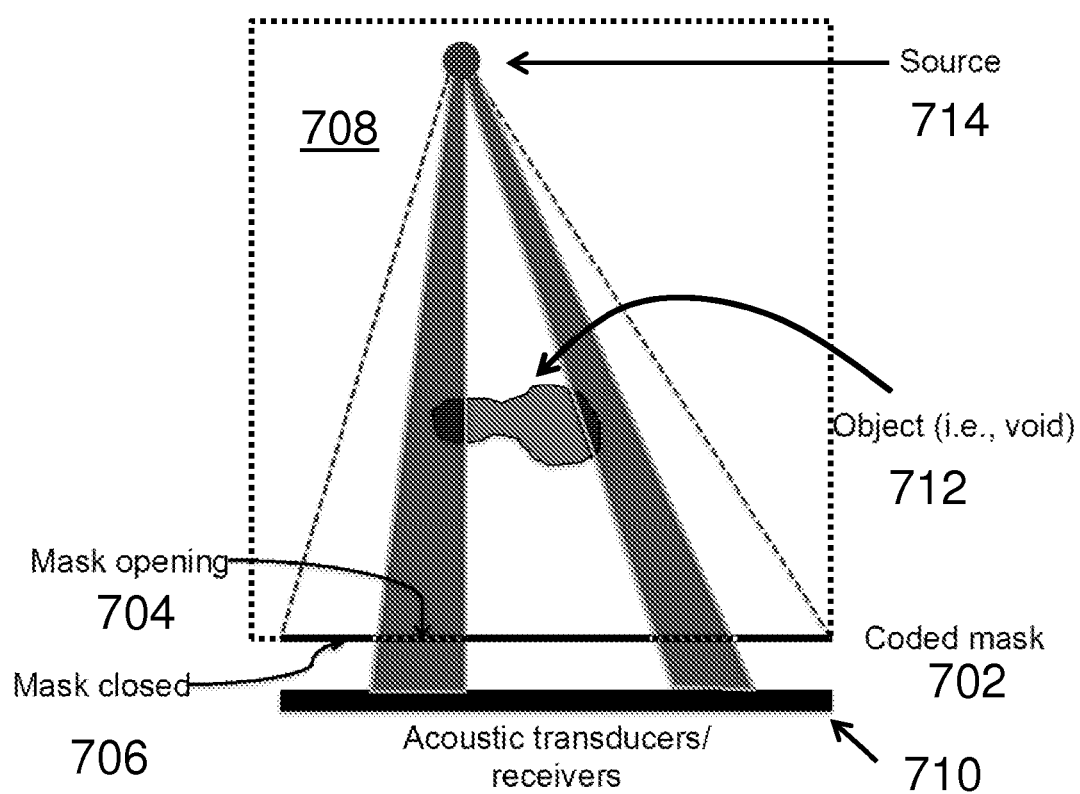
FIG. 7 is a schematic illustrating a configuration for using coded apertures in accordance with the various embodiments.

FIG. 7 is a schematic illustrating a configuration for using coded apertures in accordance with the various embodiments. As shown in FIG. 7, a coded mask 702 is provided with open portions 704 and closed portions 706, wherein the coded mask 702 is positioned between the volume of interest 708 and the beamformer array 710 consisting of transmitting elements and receiver elements. In other embodiments, the pattern can be generated by enabling a particular set of receivers in beamformer array 710.

In embodiments where a coded mask 702 is provided via a physical mask, the physical mask can be utilized in a variety of ways. In some embodiments, the physical mask can be permanent, where transmitter elements and receiver elements are placed to coincide with opening in the mask. Alternatively, the transmitter elements can be placed at the periphery of the physical mask and the receiver elements can be placed to coincide with the openings of the physical mask. In other embodiments, the physical mask can be moved during operation. That is, during transmission of the acoustic beam, the physical mask can be mechanically moved. During the detection phase, the physical mask can be mechanically moved back into place such that the receiver elements for the pattern of interest coincide with the openings in the physical mask.

As to the physical mask itself, it can be constructed from a variety of ultrasonic absorbing materials and surfaces. For example, certain plastics, composites, fiberglass, fibers, and porous forms thereof have sound absorbing properties. In some cases, the material can be selected to be opaque with respect to all frequencies. However in other cases, the selection of the actual type of material can be based on the characteristics of the acoustic beams and reflected acoustic waves to ensure that the mask only transmits acoustic waves of interest to the receiver elements. Additional a combination of materials can be used. For example, a mask can be formed by layering alternating polymer and high density (e.g., lead or tungsten) materials to form a composite. Similarly a panel can be formed using micro-perforations in which the perforated volumes consist of polymers or other absorbers.

In some embodiments, the attenuation caused by gaps and voids can be used advantageously to form a mask. In particular, the mask can be configured to provide one or more chambers that can be selectively filled with a liquid acoustic coupling material (e.g., water) or a gas (e.g., air). Thus, when these chambers are filled with the liquid, they have transmitting properties. In contrast, when filled with air, they would have attenuating properties. Thus, by selective filling of such chambers with a gas or liquid, a physical mask can be defined without the necessity to have a mechanism for physically removing the mask.

If one adds an object (e.g., object 712 in volume of interest 708) between a source 714 (i.e., a point that is illuminated) and the coded mask 702, then the problem can be formulated as follows:

$$P = \delta * O * M = O * M \tag{2}$$

where O is the object (e.g., a void in the grout, a gap or foreign object between the grout and the metal plate, etc.). Consequently, a decoding kernel K can be designed in order to deconvolute the signal. More precisely K satisfies $$K * M = H \approx \delta \tag{3}$$

so that one can estimate the attenuation associated with the object by convolving K with the measured shadowgram:

$$\hat{O} = P * K = O * M * K = O * H \approx O * \delta = O \tag{4}$$

As documented by Chang et. al. in "Coded Aperture Imaging of Gamma-Rays Using Multiple Pinhole Arrays and Multiwire Proportional Chamber Detector," Nuclear Science, IEEE Transactions on, vol. 22, no. 1, pp. 374-378 (1975), Weiss in "Nonredundant Point Distribution for Coded Aperture Imaging with Application to Three-Dimensional On-Line X-Ray Information Retrieving," Computers, IEEE Transactions on, vol. C-24, no. 4, pp. 391-394 (1975), and Mu and Liu in "Aperture collimation correction and maximum-likelihood image reconstruction for near-field coded aperture imaging of single photon emission computerized tomography," Medical Imaging, IEEE Transactions on, vol. 25, no. 6, pp. 701-711 (2006), each of which is incorporated by reference in their entirety, the kernel K can be resized in order to reconstruct 2D slices of the object and different depths. This is illustrated with respect to FIG. 8.

Figure 8:
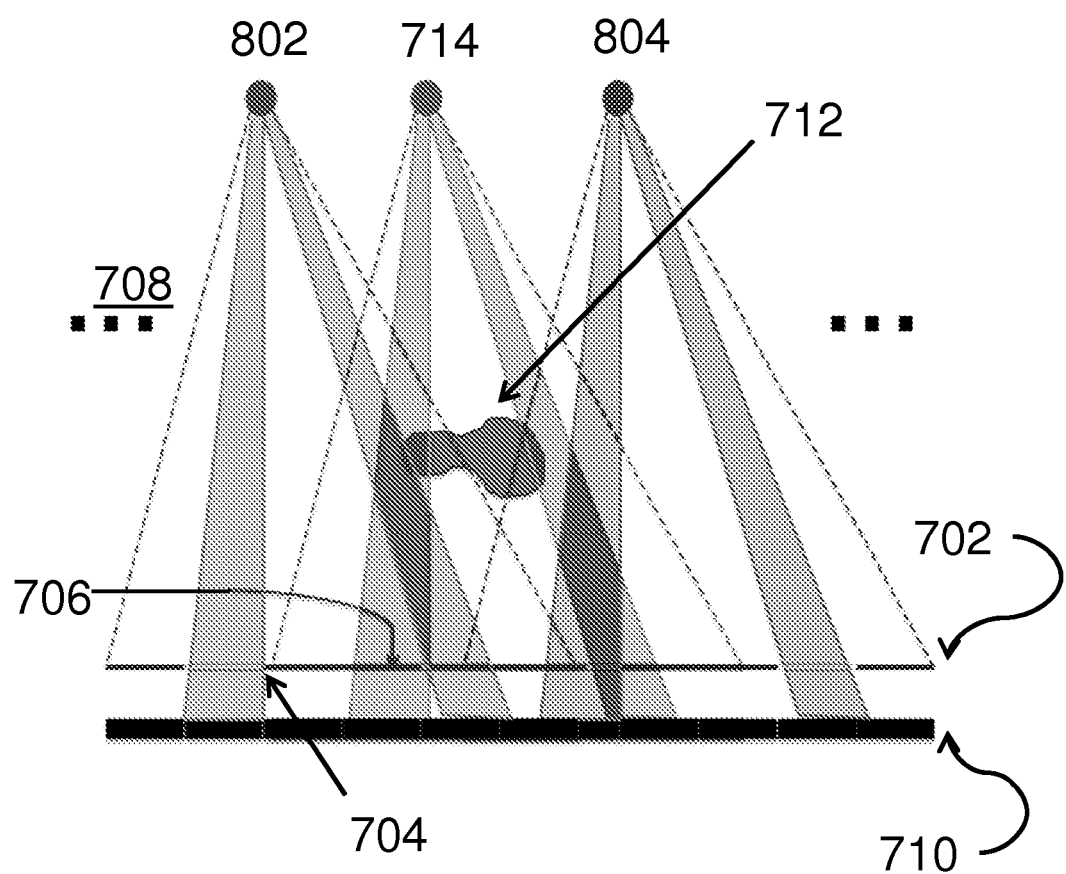
FIG. 8 is a schematic illustrating how the configuration of FIG. 7 can be utilized for collecting 2D slices.

FIG. 8 is a schematic illustrating how the configuration of FIG. 7 can be utilized for collecting 2D slices. As shown in FIG. 8, the imaging system can be translated (schematically illustrated by additional illumination of points 802 and 804) in order to collect depth slices of neighboring regions of the volume of interest 708. Note that complementary images can also be obtained by steering the beams across a plane at a given depth. By allowing overlapping between the neighbor depth slices, the images can be stitched together in order to generate a full 3D reconstruction of the material.

Such stitching can occur in a variety of ways. For example, if two images have overlapping regions, then, both should contain similar features. One can use any feature matching algorithm (e.g., SIFT) to find the equivalent features and the orientation of the features. With this information the images are translated and rotated, so that the equivalent areas are perfectly aligned. The aligned images are merged together. A discussion of stitching methods suitable for use in the various embodiments can be found in Brown et al., "Automatic Panoramic Image Stitching using Invariant Features", International Journal of Computer Vision, 74(1), pp. 59-73 (2007), and in Juan et al., "A Comparison of SIFT, PCA-SIFT and SURF", International Journal of Image Processing, 3(4), pp. 143-152 (2009), the contents of which are herein incorporated by reference in their entirety.

Coded Source Reconstruction. Similarly to coded aperture reconstruction, the beams from the beamformer array can be focused at different locations (i.e., different points in the volume of interest). The locations can be selected to generate a coded pattern M, as with the coded aperture mask. The coded source pattern can be generated as follows. The beamformer array focuses the beams at a particular point in space and the receivers detect the reflected wave intensity from that point. Then, the beamformer array focuses the beam on the next point in the pattern and again measures the reflected wave intensity. This process is repeated until all of the points in the pattern have been illuminated. Finally, all the echo signals corresponding to the measured reflected wave intensities are added together to form the coded shadowgram.

An alternative approach would be to generate the coded source by steering subsets of the beamformer array at the desired code locations and measure the echo signals generated from this configuration.

In the case of with approach, the 2D reconstruction and the 3D stitching used for coded apertures also apply for the coded source approach.

Filtered Back Projection Reconstruction. As noted above, large changes in sound attenuation characteristics are typically expected where there is a discontinuity in materials. For example, a higher amount of reflection is typically expected from regions in a volume of interest where there is a large change in refraction index. Therefore, if there is a void in the grout between an illuminated point and a transmitter/receiver element, the received signal at the transmitter/receiver element will be significantly affected. This is schematically illustrated in FIG. 9.

Figure 9:
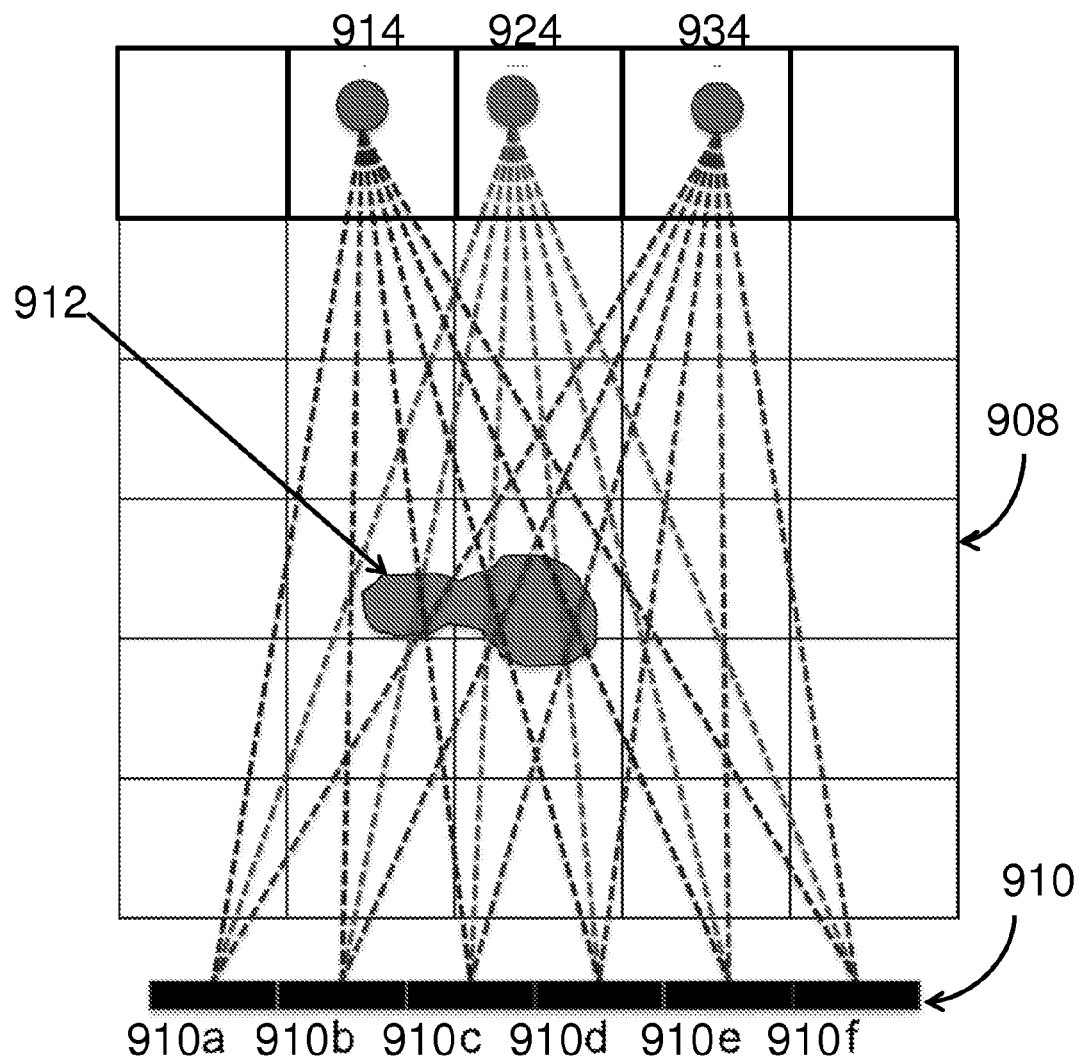
FIG. 9 is a schematic illustrating the effect of an object in a volume of interest with various illuminated points with respect to a beamforming array including a plurality of transmitter/receiver elements in accordance with the various embodiments.

FIG. 9 is a schematic illustrating the effect of an object 912 in volume of interest 908 with various illuminated points 914, 924, 934 with respect to a beamforming array 910 including a plurality of transmitter/receiver elements 910a-f. The points 914, 924, and 934 can be illuminated as described above with respect to FIGS. 1 and 2. The result of the illumination is the generating of reflected waves 916 from point 914, beams 926 from point 924, and beams 936 from point 934, where each of the beams is at least initially directed towards one of transmitter/receiver elements 910a-f.

However, the presence of object 912 will affect the reflected wave intensity measured at transmitter/receiver elements 910a-f. For example, since there will be a higher amount of reflection at the boundary between the object 912 and the grout defining the volume of interest 908, the reflected waves (from point 914) traveling through object 912 will be attenuated. For example, the reflected wave intensity received at transmitter/receiver elements 910c, 910d, and 910e will be smaller than the reflected wave intensity received at transmitter/receiver elements 910a, 910b, and 910f. The reason is that a larger portion of the waves from point 914 traversing object 912 will be reflected away from transmitter/receiver elements 910c, 910d, and 910e due to the reflection at the grout/object boundary. A similar difference in received signals from points 924 and 934 would be observed.

Filtered Back Projection (FBP) can be used to address the problem described above. In operation, the unknown material is discretized in equally spaced cells (for 2D, cubes for 3D). Then, the traces (i.e., beam paths) between the points and the transmitter/receiver elements are computed. Consequently, one can compute which cells are in the path of each trace. If the receiver for a particular trace measured E units intensity, these units are distributed across the intersected cells. The E units can be distributed uniformly or by an interpolation coefficient $p_i$ that represents how much the trace intersects the cell i, where $$\Sigma_{i=1}^{N} p_i = 1 \quad (5)$$

and N is the number of intersected cells. This process is repeated for all traces and focus points. It should be noted that cells where the attenuation of the material changes should end with lower counts than cells where no attenuation changes occur. Combining the phase array steering measurements with measurements at different positions of the imaging device can enhance the accuracy of this approach.

The concepts can be adapted to various industries and applications, including oil/gas well cement inspection by incorporating the transmitter elements and receiver elements in a carriage that can be circumferentially scanned to map the cement image. The scan can be then moved axially to create a tomographic representation of the entire cement structure. This is illustrated with respect to FIGS. 10 and 11.

Figure 10:
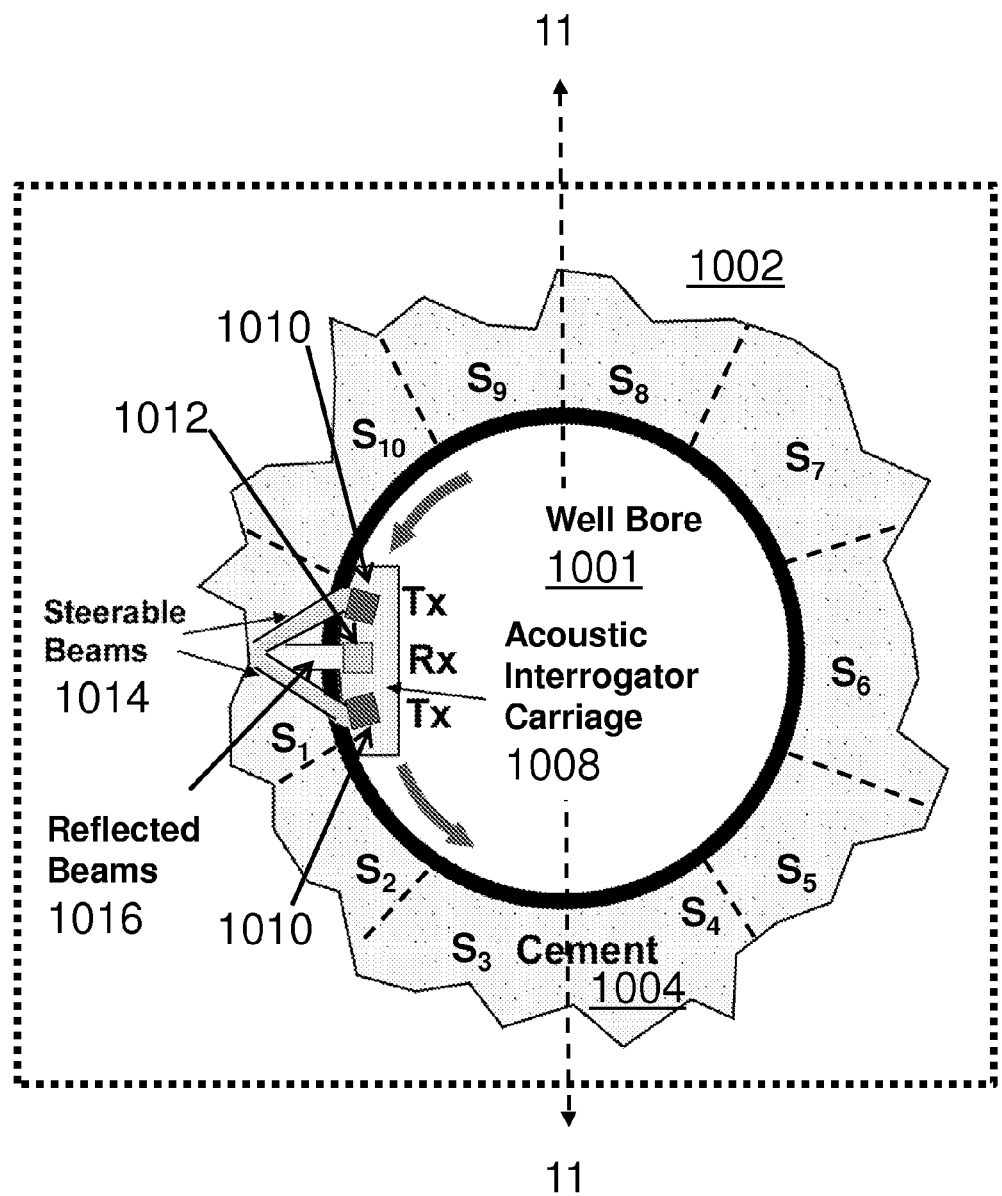
FIG. 10 illustrates inspection of a well using a carriage configured in accordance with the various embodiments of the invention.
Figure 11:
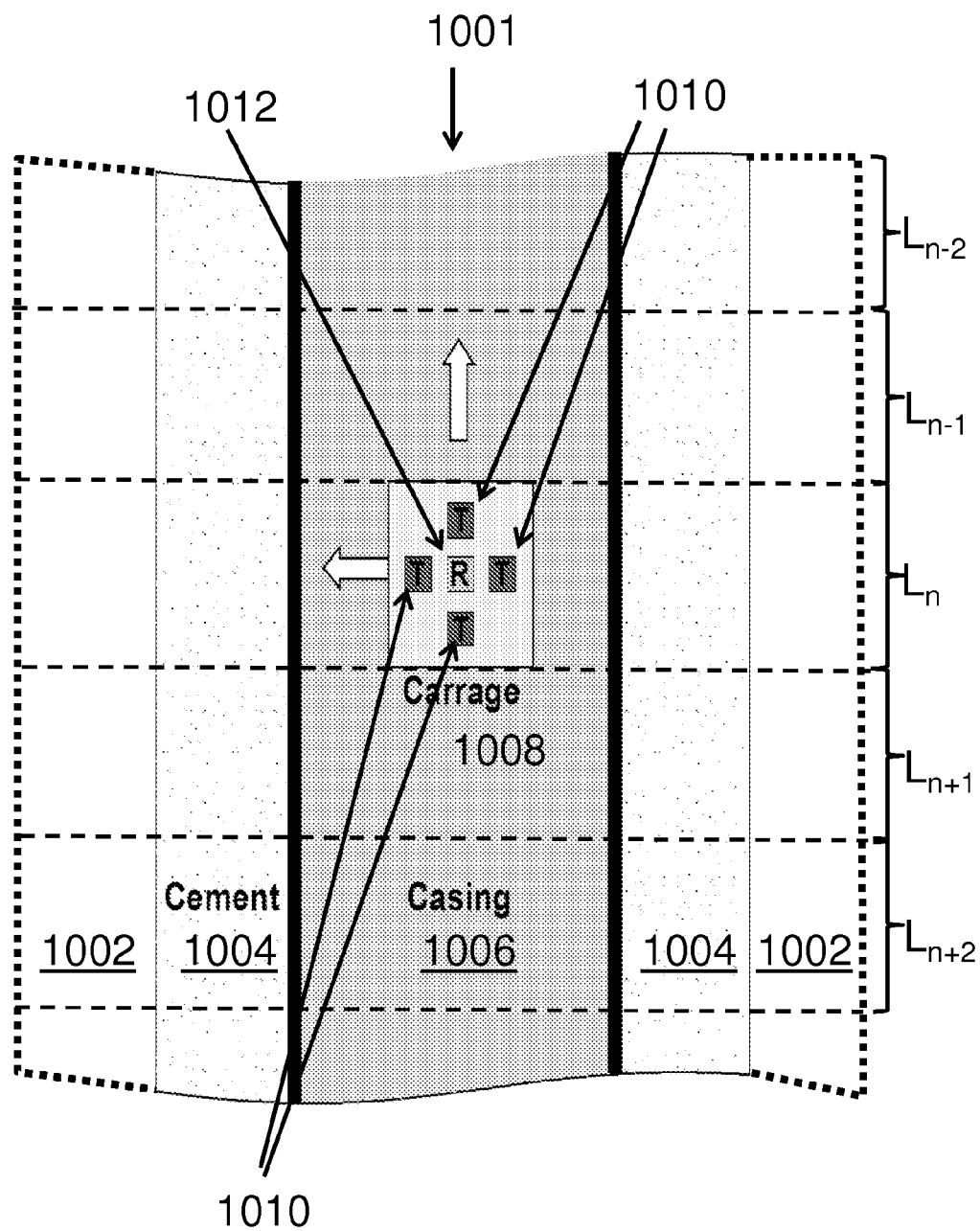
FIG. 11 shows a cross-section view of the well of FIG. 10 along cutline 11-11.

FIG. 10 shows scanning of a well 1000 using a carriage 1008 configured in accordance with the various embodiments of the invention. FIG. 11 shows a cross-section view of the well 1000 of FIG. 10 along cutline 11-11. FIG. 10 illustrates circular or lateral scanning of the well 1000, while FIG. 11 illustrates the axial scanning of the well 1000.

As shown in FIGS. 10 and 11, the well 1000 consists of a rock face 1002 having disposed therein grout 1004 (shown as cement in FIGS. 10 and 11). Further a casing 1006 is disposed on the grout 1004 to define the well bore 1001.

As noted above, a carriage 1008 is provided for inspection of the well 1000. The carriage consists of a beamformer array defined by beamformers 1010, each capable of generating steerable or directed acoustic beams 1014. The carriage also includes one or more receiver elements 1012 for detecting reflected waves 1016. The operation of the beamformers 1010 and the beamformer array is substantially similar to that discussed above with respect to FIGS. 1-6. Although carriage 1008 is illustrated with a particular configuration of beamformers 1010 and receiver elements 1012, this is solely for illustrative purposes. In the various embodiments, the carriage 1008 can include any number and arrangement of transmitter elements and receiver elements, as described above.

The carriage 1008 can also include additional functionality. For example, the carriage 1008 can include a computing device (not shown) to control the movement and operation of beamformers 1010 and receiver elements 1012 and to analyze or process collected data as needed. However, in some embodiments, the controller for the carriage can also be in a computing device located external to the carriage 1008 and the carriage 1008 can be communicatively coupled to such an external computing device via wired or wireless communications links.

In operation, the carriage 1008 is first tethered from or attached to the casing 1006 to perform any necessary scanning. Any suitable methods for tethering or attaching the carriage 1008 to the casing 1006 can be used in the various embodiments. In some embodiments, the surface of the carriage 1008 in contact with the casing 1006 can be configured to have a same shape so as to allow for maximum transfer of acoustic energy. However, in many cases it is unlikely that such shapes would be the same and voids are likely to occur. Such voids would typically attenuate any acoustic signals, severely affecting the sensitivity of the scan. Accordingly, in other embodiments, an acoustic coupling material (not shown) can be inserted between the carriage 1008 and the casing 1006. For example, an acoustically conductive gel, liquid, or other material can be provided between the carriage 1008 and the casing 1006. It should be noted that in some cases, a cleaning of the well may be required, as remaining residue could attenuate acoustic signals, even with the coupling medium in place.

Once attached to the casing 1006, the carriage 1008 can begin scanning. That is, the carriage 1008 can be positioned and can illuminate a number of points in a selected portion of the well via adjustment or steering of a direction of the beams 1014 from beamformers 1010. For example, as shown in FIGS. 10 and 11, the carriage 1008 can be positioned to scan one of slices $S_1$-$S_{10}$ in one of layers L. In FIGS. 10 and 11, the carriage 1008 is positioned to scan slice $S_1$ in layer $L_n$. It should be noted that the number and size of slices and layers in FIGS. 10 and 11 is presented solely for illustrative purposes. Thus, more or less slices and layer than shown can be provided. Further, the size of such slices and layers can be larger or smaller than shown in FIGS. 10 and 11.

In response to the illumination of the points in the selected portion, the reflected waves 1016 can be collected by the receiving elements 1012. Thereafter, the carriage 1008 can be repositioned to scan a different portion of the well 1000. For example, the carriage 1008 can be repositioned for scanning a next one of slices $S_1$-$S_{10}$. This circular scanning can continue until all of slices $S_1$-$S_{10}$ have been scanned. At this point, then the carriage 1008 can be repositioned, vertically higher or lower, to scan slices in a different one of layers L.

During the scanning or once the scanning is complete, an image of the scanned portions for the well 1000 can then be generated, as discussed above with respect to FIGS. 7, 8, and 9.

Figure 12A:
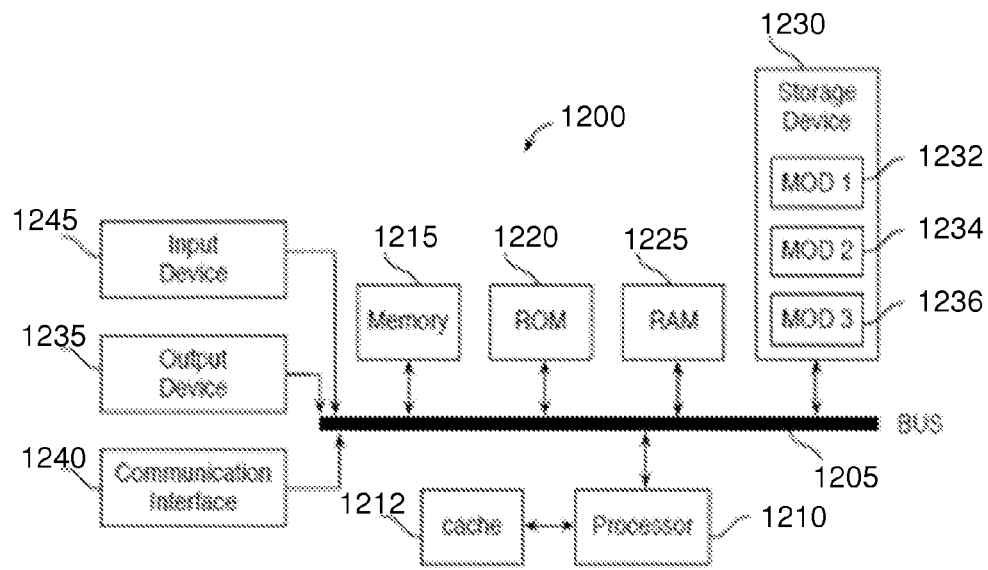
FIG. 12A and FIG. 12B illustrate exemplary possible configurations for a computing device for implementing the various embodiments.
Figure 12B:
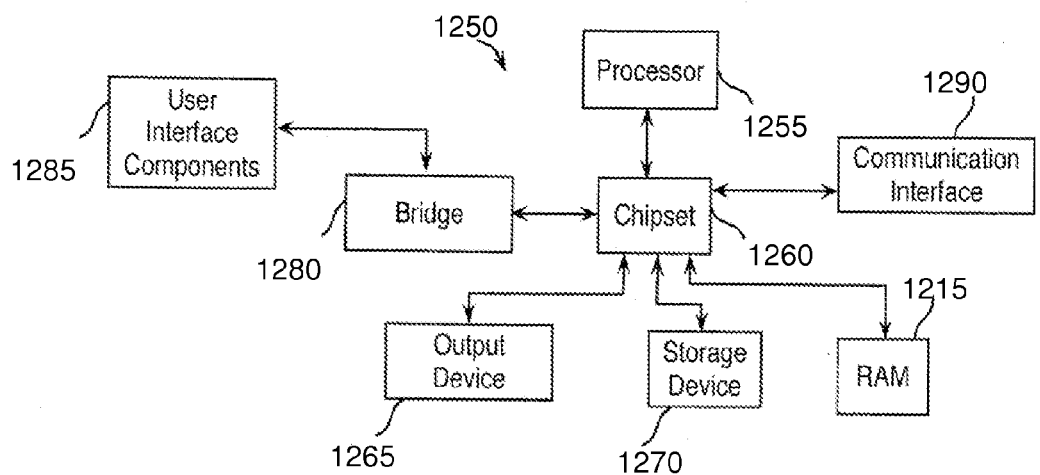

FIG. 12A and FIG. 12B illustrate exemplary possible configurations for a computing device for implementing the various embodiments. The more appropriate embodiment will be apparent to those of ordinary skill in the art when practicing the present technology. Persons of ordinary skill in the art will also readily appreciate that other system embodiments are possible.

FIG. 12A illustrates a conventional system bus computing system architecture 1200 wherein the components of the system are in electrical communication with each other using a bus 1205. Exemplary system 1200 includes a processing unit (CPU or processor) 1210 and a system bus 1205 that couples various system components including the system memory 1215, such as read only memory (ROM) 1220 and random access memory (RAM) 1225, to the processor 1210. The system 1200 can include a cache of high-speed memory connected directly with, in close proximity to, or integrated as part of the processor 1210. The system 1200 can copy data from the memory 1215 and/or the storage device 1230 to the cache 1212 for quick access by the processor 1210. In this way, the cache can provide a performance boost that avoids processor 1210 delays while waiting for data. These and other modules can control or be configured to control the processor 1210 to perform various actions. Other system memory 1215 may be available for use as well. The memory 1215 can include multiple different types of memory with different performance characteristics. The processor 1210 can include any general purpose processor and a hardware module or software module, such as module 1 1232, module 2 1234, and module 3 1236 stored in storage device 1230, configured to control the processor 1210 as well as a special-purpose processor where software instructions are incorporated into the actual processor design. The processor 1210 may essentially be a completely self-contained computing system, containing multiple cores or processors, a bus, memory controller, cache, etc. A multi-core processor may be symmetric or asymmetric.

To enable user interaction with the computing device 1200, an input device 1245 can represent any number of input mechanisms, such as a microphone for speech, a touch-sensitive screen for gesture or graphical input, keyboard, mouse, motion input, speech and so forth. An output device 1235 can also be one or more of a number of output mechanisms known to those of skill in the art. In some instances, multimodal systems can enable a user to provide multiple types of input to communicate with the computing device 1200. The communications interface 1240 can generally govern and manage the user input and system output. There is no restriction on operating on any particular hardware arrangement and therefore the basic features here may easily be substituted for improved hardware or firmware arrangements as they are developed.

Storage device 1230 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1225, read only memory (ROM) 1220, and hybrids thereof.

The storage device 1230 can include software modules 1232, 1234, 1236 for controlling the processor 1210. Other hardware or software modules are contemplated. The storage device 1230 can be connected to the system bus 1205. In one aspect, a hardware module that performs a particular function can include the software component stored in a computer-readable medium in connection with the necessary hardware components, such as the processor 1210, bus 1205, display 1235, and so forth, to carry out the function.

FIG. 12B illustrates a computer system 1250 having a chipset architecture that can be used in executing the described method and generating and displaying a graphical user interface (GUI). Computer system 1250 is an example of computer hardware, software, and firmware that can be used to implement the disclosed technology. System 1250 can include a processor 1255, representative of any number of physically and/or logically distinct resources capable of executing software, firmware, and hardware configured to perform identified computations. Processor 1255 can communicate with a chipset 1260 that can control input to and output from processor 1255. In this example, chipset 1260 outputs information to output 1265, such as a display, and can read and write information to storage device 1270, which can include magnetic media, and solid state media, for example. Chipset 1260 can also read data from and write data to RAM 1275. A bridge 1280 for interfacing with a variety of user interface components 1285 can be provided for interfacing with chipset 1260. Such user interface components 1285 can include a keyboard, a microphone, touch detection and processing circuitry, a pointing device, such as a mouse, and so on. In general, inputs to system 1250 can come from any of a variety of sources, machine generated and/or human generated.

Chipset 1260 can also interface with one or more communication interfaces 1290 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 1255 analyzing data stored in storage 1270 or 1275. Further, the machine can receive inputs from a user via user interface components 1285 and execute appropriate functions, such as browsing functions by interpreting these inputs using processor 1255.

It can be appreciated that exemplary systems 1200 and 1250 can have more than one processor 1210 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. An inspection system, comprising:
a plurality of acoustic beamformers, each of the plurality of acoustic beamformers comprising a plurality of acoustic transmitter elements;
at least one controller, the at least one controller configured for causing each of the plurality of acoustic beamformers to generate a plurality of acoustic beams directed to a plurality of points in the volume of interest during a first time and to generate an image of the volume of interest based on reflected waves associated with the plurality of acoustic beams; and
a plurality of acoustic receiver elements,
wherein the at least one controller causes the plurality of beamformers to generate a portion of the plurality of acoustic beams associated with each one of the plurality of point so that each of the plurality of beamformers provides a separate acoustic beam traveling in a separate direction to the one of the plurality of points,
wherein the at least one controller is further configured for operating at least one of the plurality of acoustic beamformers during a first time, obtaining echo signals corresponding to a reflected wave intensity detected at the plurality of acoustic receiver elements during a second time after the first time, repeating the operating and the obtaining for a plurality of other points in the volume of interest, combining the echo signals for all points in the volume of interest to yield combined signals, and generating an image of the volume of interest based on the combined signals,
wherein the generating comprises applying a coded aperture reconstruction algorithm for the generating of the image using a shadow gram,
wherein the shadowgram for the coded aperture reconstruction algorithm is based on the combined signals and a pattern of the plurality of acoustic receiver elements.

2. The inspection system of claim 1, wherein the at least one controller causes each one of the plurality of acoustic beamformers to generate each separate acoustic beam by operating the plurality of acoustic transmitter elements in the one of the plurality of beamformers using at least one of different timings and different phases among the plurality acoustic transmitter elements.

3. The inspection system of claim 1, wherein the plurality of acoustic receiver elements are intermixed among the plurality of acoustic transmitter elements.

4. The inspection system of claim 1, wherein at least a portion of the plurality of acoustic transmitter elements comprise acoustic transceiver elements, wherein the acoustic transceiver elements define the plurality of acoustic receiver elements.

* * * * *